(12) United States Patent
Dreyfus et al.

(10) Patent No.: US 8,563,280 B2
(45) Date of Patent: Oct. 22, 2013

(54) NICOTIANAMINE-DERIVED METALLOPHORE AND PROCESSES FOR PRODUCING SAME

(75) Inventors: Cyril Dreyfus, Le Crès (FR); David Pignol, Manosque (FR); Pascal Arnoux, Pierrerue (FR); Florine Cavelier, Castelnau le Lez (FR); Manuel Larrouy, Montpellier (FR); Jean Martinez, Caux (FR)

(73) Assignees: Commissariat a l'Energie Atomique et aux Energies Alternatives, Paris (FR); Centre National de la Recherche Scientifique, Paris (FR)

( * ) Notice: Subject to any disclaimer, the term of this patent is extended or adjusted under 35 U.S.C. 154(b) by 12 days.

(21) Appl. No.: 13/260,605

(22) PCT Filed: Mar. 26, 2010

(86) PCT No.: PCT/FR2010/000261
§ 371 (c)(1),
(2), (4) Date: Dec. 20, 2011

(87) PCT Pub. No.: WO2010/112697
PCT Pub. Date: Oct. 7, 2010

(65) Prior Publication Data
US 2012/0095262 A1    Apr. 19, 2012

(30) Foreign Application Priority Data
Mar. 31, 2009    (FR) ..................... 09 01574

(51) Int. Cl.
*C12P 13/00*    (2006.01)
*C07C 229/26*    (2006.01)

(52) U.S. Cl.
USPC ........................................... 435/128; 562/565

(58) Field of Classification Search
CPC ...... C07C 227/18; C07C 229/16; C12P 13/00
See application file for complete search history.

(56) References Cited

U.S. PATENT DOCUMENTS

2007/0043018 A1    2/2007  Aoyagi

OTHER PUBLICATIONS

Dreyfus et al, Proceedings of the National Academy of Sciences of the United States of America, Crystallographic Snapshots of Iterative Substrate Translocations During Nicotianamine Synthesis in Archaea, 2009, 106(38), pp. 16180-16184.*
Written Opinion for International Application PCT/FR2010/000261 (undated).
Dreyfus, C. et al., *Expression, Purification, Crystallization and Preliminary X-ray Analysis of an Archaeal Protein Homologous to Plant Nicotianamine Synthase*, Acta Crystallographica Section F, vol. 64, (2008), pp. 933-935.

* cited by examiner

*Primary Examiner* — Paul A Zucker
(74) *Attorney, Agent, or Firm* — Alston & Bird LLP

(57) ABSTRACT

The invention relates to a nicotianamine derivative and to a process for chemical or enzymatic synthesis thereof. The nicotianamine derivative has the following formula (I). The invention finds use in the pharmacy field in particular.

(I)

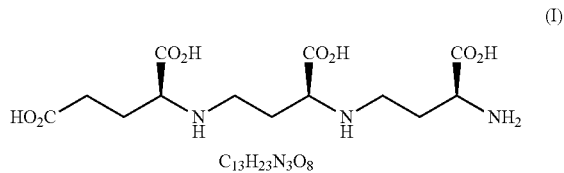

$C_{13}H_{23}N_3O_8$

4 Claims, No Drawings

NICOTIANAMINE-DERIVED METALLOPHORE AND PROCESSES FOR PRODUCING SAME

FIELD OF THE INVENTION

The invention relates to a nicotianamine derivative and to a process for chemical or enzymatic synthesis thereof.

BACKGROUND

Nicotianamine (NA) is a non-proteinogenic amino acid present in all higher plants. In vitro, NA can chelate many metal ions (Fe, Mn, Zn, Ni, Cu) and, in vivo, it plays an important role in the homeostasis of these metals in plants.

In addition, it has been shown that nicotianamine has antihypertensive properties through the inhibition of angiotensin I-converting enzyme (ACE) (Kinoshita et al., Biosci Biotechnol Biochem, 57, 1107-10, 1993; Shimizu et al., J Nutr Sci Vitaminol (Tokyo), 45, 375-83, 1999; Wada et al., Biosci Biotechnol Biochem, 70, 1408-15, 2006).

In higher plants, nicotianamine biosynthesis is catalyzed by the nicotianamine synthase (NAS; EC 2.5.1.43) and is the result of the trimerization of three S-adenosyl methionine (SAM) molecules. Sequence database searches have made it possible to detect putative homologs of NAS in organisms other than higher plants, in particular in fungi and archaea (Trampczynska et al., FEES Lett, 580, 3173-8, 2006; Herbik et al., Eur J Biochem, 265, 231-9, 1999). The presence of a functional NAS has also been demonstrated in the filamentous fungus *Neurospora crassa* (Trampczynska et al., FEBS Lett, 580, 3173-8, 2006). Recently, the team of the inventors (Dreyfus et al., Acta Cryst., F64, 933-5, 2008) has expressed, in *E. coli*, an enzyme of the archaeon *Methanothermobacter thermoautotrophicus* (MTH675; GenBank NP_275817), which is a homolog of eukaryotic NASs. This enzyme will hereinafter be referred to as MtNAS.

SUMMARY

In continuing their studies on the characterization of this enzyme *Methanothermobacter thermoautotrophicus*, the inventors have found a novel molecule synthesized by this enzyme.

This molecule, hereinafter referred to as thermonicotianamine (thNA), comprises an additional carboxylic group compared with nicotianamine.

This nicotianamine derivative has the following formula:

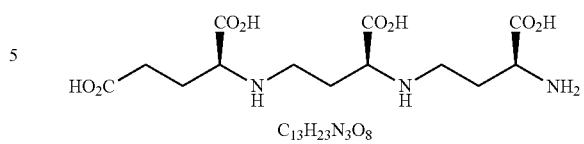

This derivative can advantageously be synthesized by a chemical process which comprises the following steps:
a) protection of the amine function of the α-tert-butyl ester of L-aspartic acid,
b) reduction of the carboxylic function of the compound obtained in step a),
c) halogenation of the alcohol function of the compound obtained in step b), preferably with iodine,
d) protection-activation of the amine function of di-tert-butyl ester of L-glutamic acid,
e) alkylation of the compound obtained in step d), with the compound obtained in step c),
f) deprotection followed by protection-activation of the amine function of the compound obtained in step e),
g) alkylation of the compound obtained in step f), with the compound obtained in step c), and
h) total deprotection of the compound obtained in step g).

Thermonicotianamine can also be synthesized enzymatically, by incubation of the substrates SAM and glutamic acid (GLU) in the presence of the MtNAS enzyme of *Methanothermobacter*, or one of its orthologs in another archaeon, purified as described by Dreyfus et al. (2008, mentioned above).

It is also possible to synthesize it using cultures of thermoautotrophicus or of another archaeon expressing an ortholog of MtNAS, or using a host cell (for example *E. coli*) transformed with a polynucleotide encoding MtNAS or one of its orthologs, and expressing said enzyme.

The nicotianamine derivative according to the invention can advantageously be used as a replacement for or in addition to nicotianamine itself in all the applications of nicotianamine.

The chemical process for synthesizing the nicotianamine derivative of the invention is carried out according to the reaction scheme hereinafter:

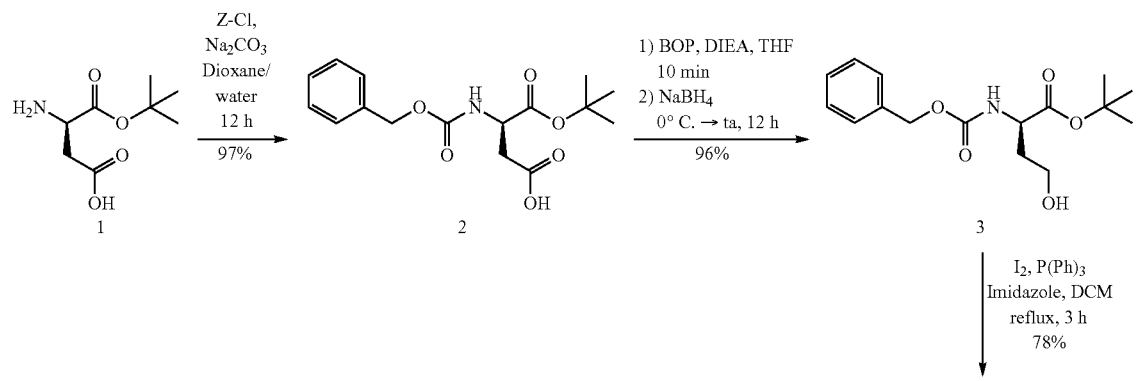

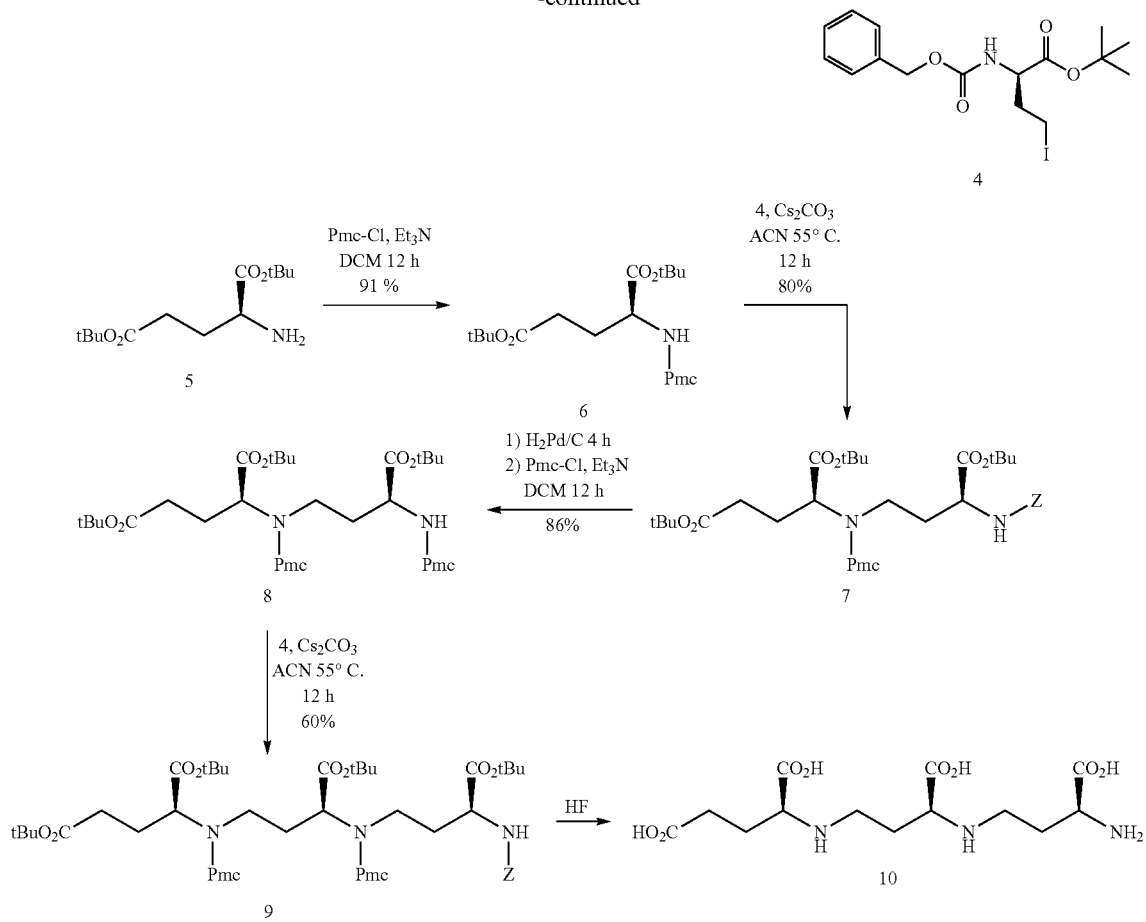

More specifically, the nicotianamine derivative according to the invention is produced starting from, on the one hand, the α-tert-butyl ester of L-aspartic acid, which is a commercially available product, and, on the other hand, the di-tert-butyl ester of L-glutamic acid, which is also a commercially available product.

DETAILED DESCRIPTION

The starting compound is therefore the α-tert-butyl ester of L-aspartic acid, which is the compound named 1 having the following formula:

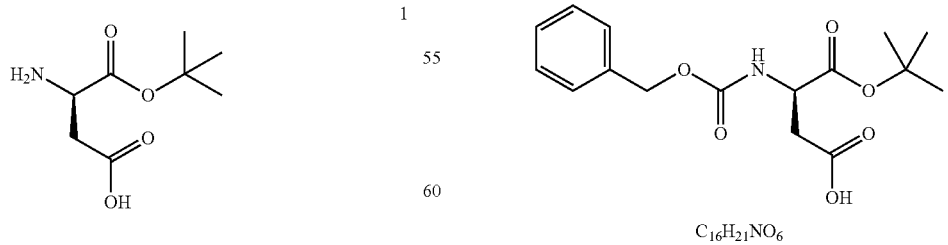

1

The protection of the amine of this compound is then carried out in the following way:

Sodium bicarbonate (13 g, 159 mmol) and, over the course of a period of 2 hours, a solution of benzyl chloroformate (11.8 mL, 69 mmol) in dioxane (70 mL) are added to a solution of α-tert-butyl aspartate (10 g, 53 mmol) in a water/dioxane mixture (2/1) (170 mL). Stirring is carried out overnight at ambient temperature. The reaction medium is washed with ethyl acetate (3×200 mL), and then acidified at 0° C. with a 6N hydrochloric acid solution until pH=2. The aqueous phase is extracted with ethyl acetate (3×200 mL). The combined organic phases are washed with brine (200 mL) and then dried over anhydrous magnesium sulfate and concentrated so as to obtain the compound 2 in the form of a colorless oil (16.7 g, 97.96).

The compound 2 having the following formula is obtained:

2

$C_{16}H_{21}NO_6$

Rf: (CHCl$_3$/MeOH/AcOH 37%)=0.68

HPLC: 1.56 min

MS: [M+H]$^+$, 324.1; [M+H−tBu]$^+$, 268.1

¹H NMR (CDCl₃, 300 MHz): 1.45 (s, 9H, 1 tBu); 2.95 (dd, 2H, J=4.5 and 14 Hz, CH$_{2\beta}$); 4.55 (q, 1H, J=4.3 Hz, CH$_\alpha$); 5.10 (s, 2H, CH$_2$Ph); 5.8 (d, 1H, J=8 Hz, NH); 7.35 (m, 5H, arom); 10.7 (bs, 1H, COOH)

¹³C NMR (CDCl₃, 75 MHz): 27.79; 36.73; 50.75; 67.12; 82.83; 128.11; 128.20; 128.53; 136.12; 156.06; 169.46; 176.25.

The reduction of the carboxylic function of the compound 2 is then carried out in the following way:

Diisopropylethylamine (10.5 mL, 60.4 mmol) is added to a suspension of 2 (15 g, 46.4 mmol) and of BOP (27 g, 60.4 mmol) in anhydrous THF. The reaction medium is left to stir vigorously for 10 minutes until it turns yellow in color, and is then cooled to 0° C. for 15 minutes. Next, NaBH₄ (2.3 g, 60.4 mmol) is added to the reaction medium in small portions. The reaction mixture is left to stir vigorously overnight. The solvent is evaporated off and the residue is taken up in ethyl acetate (250 mL). The solution is washed successively with a 10% citric acid solution (3×100 mL), a saturated sodium hydrogen carbonate solution (3×100 mL) and then distilled water (2×100 mL). The organic phase is dried over anhydrous magnesium sulfate and then concentrated to give a colorless oil. The compound 3 is purified by silica gel chromatography (petroleum ether/ether: 3/7) to give a colorless oil (13.95 g, 96%).

The compound 3 having the following formula is obtained:

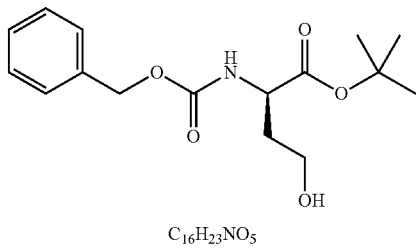

3

C₁₆H₂₃NO₅

Rf: (petroleum ether/ether: 3/7)=0.42
HPLC: 1.45 min
MS: [M+H]⁺, 310.2; [M+H-tBu]⁺, 254.1
¹H NMR (CDCl₃, 300 MHz): 1.43 (s, 9H, 1 tBu); 2.09 (dd, 2H, J=4.6 and 15.2 Hz, CH$_{2\beta}$); 3.48 (s, 1H, OH); 3.8 (m, 2H, CH$_{2\gamma}$); 4.45 (m, 1H, CH$_\alpha$); 5.10 (s, 2H, CH$_2$Ph); 5.87 (d, 1H, J=8 Hz, NH); 7.35 (m, 5H, arom)
¹³C NMR (CDCl₃, 75 MHz): 27.9; 35.45; 51.95; 58.4; 67.01; 82.44; 128.07; 128.13; 128.13; 128.31; 129.01; 136.1; 156.79; 169.46; 171.68.

The halogenation of the alcohol of the compound 3 is then carried out in the following way:

Iodine (14.3 g, 56.4 mmol), triphenylphosphine (14.8 g, 56.4 mmol) and, after 10 minutes, imidazole (9.6 g, 141 mmol) were added to a solution of the compound 3 (5.8 g, 18.8 mmol) in anhydrous dichloromethane (260 mL) under argon. The reaction medium is brought to reflux and is left to stir vigorously for 3 hours. Once the reaction mixture has returned to ambient temperature, it is washed successively with a molar solution of potassium hydrogen sulfate (3×150 mL), a saturated solution of sodium hydrogen carbonate (3×150 mL) and a 5% solution of sodium thiosulfate (3×150 mL) and with brine (150 mL). The organic phase is dried over anhydrous magnesium sulfate and then concentrated so as to give a yellow paste. The product 4 is obtained after silica gel chromatography (petroleum ether/ethyl acetate: 10/0 to 8/2) in the form of a yellow oil (6.2 g, 78%).

The compound 4 having the following formula is obtained:

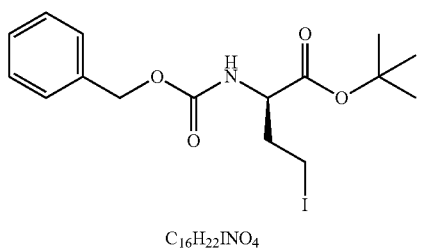

4

C₁₆H₂₂INO₄

Rf: (petroleum ether/ethyl acetate: 8/2)=0.65
HPLC:
MS: [M+Na]⁺, 442.0; [M+H]⁺, 420.1; [M+H-tBu]⁺, 364.2
¹H NMR (CDCl₃, 300 MHz): 1.45 (s, 9H, 1 tBu); 2.15-2.45 (2m, 2H, CH$_{2\beta}$); 3.15 (m, 2H, CH$_{2\gamma}$); 4.35 (m, 1H, CH$_\alpha$); 5.10 (s, 2H, CH$_2$Ph); 5.87 (d, 1H, J=8 Hz, NH); 7.35 (m, 5H, arom)
¹³C NMR (CDCl₃, 75 MHz): 16.1; 28.42; 38.45; 54.24; 56.15; 67.89; 83.59; 128.95; 129.03; 129.22; 129.34; 129.38; 136.93; 156.69; 171.03.

Separately, taking the di-tert-butyl ester of L-glutamic acid: compound 5, the protection-activation of the amine of this compound 5 having the following formula:

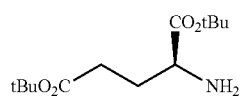

5 is carried out.

Triethylamine (0.29 mL, 2.10 mmol) is added to a solution of tert-butyl glutamate hydrochloride (0.62 g, 2.10 mmol) in anhydrous dichloromethane (20 mL). The solution is filtered and then triethylamine (0.60 mL, 4.41 mmol) and 2,2,5,6,7-pentamethylchroman sulfonyl chloride (0.7 g, 3.30 mmol) dissolved in anhydrous dichloromethane (4 mL) are added thereto over the course of a period of 2 h, with a syringe driver. The reaction medium is left to stir vigorously overnight. The reaction medium is concentrated under vacuum and then taken up in ethyl acetate (20 mL). The organic phase is successively washed with a 10% solution of citric acid (3×20 mL), with a saturated solution of sodium hydrogen carbonate (3×20 mL) and with distilled water (3×20 mL), and then dried over anhydrous magnesium sulfate and concentrated under vacuum. The sulfonamide 6 is obtained after silica gel chromatography (petroleum ether/ether 8/2) in the form of a colorless oil (1 g, 91%).

The following compound 6 is obtained:

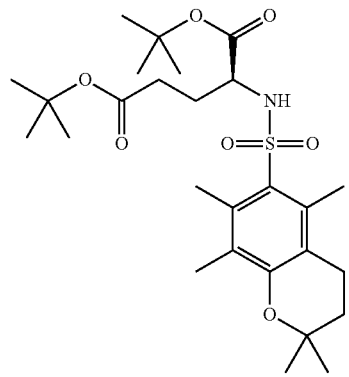

C₂₇H₄₃NO₇S

Rf: (petroleum ether/ether 6/4)=0.3
HPLC: 2.41 min
MS: [M+H]$^+$, 526.3; [M+H-tBu]$^+$, 470.2; [M+H-2 tBu]$^+$, 414.2
$^1$H NMR (CDCl$_3$, 300 MHz): 1.14-1.24 (s, 9H, 1 tBu); 1.22-1.24 (2s, 6H, 2 CH$_3$); 1.36 (s, 9H, 1 tBu); 1.70-1.99 (m, 4H, CH$_2$ meta, CH$_{2\beta}$); 2.03 (s, 3H, CH$_3$); 2.27-2.33 (m, 2H, CH$_{2\gamma}$); 2.47-2.49 (2s, 6H, 2 CH$_3$ ortho); 2.54-2.59 (t, 2H, J=6.8 and 6.8 Hz, CH$_2$); 3.66-3.67 (m, 1H, CH$_\alpha$); 5.20-5.23 (d, 1H, J=9.4 Hz, NH)
$^{13}$C NMR (CDCl$_3$, 75 MHz): 11.42; 12.17; 14.11; 17.30; 18.25; 19.42; 20.42; 21.50; 22.60; 26.52; 26.81; 27.60; 28.05; 28.60; 29.04; 29.68; 30.97; 32.67; 55.09; 73.91; 76.61; 80.53; 82.29; 118.32; 124.60; 128.43; 136.42; 136.60; 154.65; 171.07; 171.97.

The alkylation of the compound 6 with the compound 4 is then carried out in the following way:

Cesium carbonate (0.75 g, 2.31 mmol) is added to a solution of the sulfonamide 6 (0.81 g, 1.54 mmol) in anhydrous acetonitrile (20 mL). The reaction medium is stirred vigorously for 30 minutes, and then heated to 55° C. Next, the iodinated compound 4 (0.64 g, 1.54 mmol) in solution in anhydrous acetonitrile (5 mL) is added very slowly with a syringe driver. The reaction medium is left to stir vigorously at 55° C. overnight. The reaction medium is evaporated under vacuum and then taken up in ethyl acetate (20 mL). The organic phase is successively washed with brine (3×20 mL) and with distilled water (3×20 mL), and then dried over anhydrous magnesium sulfate and concentrated under vacuum. The sulfonamide 7 is obtained after silica gel chromatography (petroleum ether/ether 7/3 then dichloromethane/ether 99/1 to 98/2) in the form of a colorless oil (1 g, 80%).

The compound 7 having the following formula is obtained:

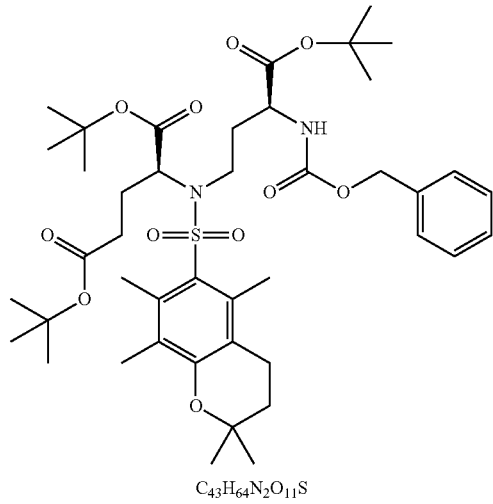

C$_{43}$H$_{64}$N$_2$O$_{11}$S

Rf: (petroleum ether/ether 6/4)=0.57
HPLC: 2.72 min
MS: [M+Na]$^+$, 839.6; [M+H]$^+$, 817.6; [M+H-tBu]; 761.5; [M+H-2 tBu]$^+$, 705.5; [M+H-3 tBu]$^+$, 649.5
$^1$H NMR (CDCl$_3$, 300 MHz): 1.17-1.36 (5s, 33H, 3 tBu, 2 CH$_3$); 1.70-2.00 (m, 6H, CH$_2$, CH$_{2\beta}$, CH$_{2\beta'}$); 2.03 (s, 3H, CH$_3$ meta); 2.17-2.20 (m, 2H, CH$_{2\gamma}$); 2.41-2.42 (2s, 6H, 2 CH$_3$ ortho); 2.52-2.56 (t, 2H, J=6.8 and 6.3 Hz, CH$_2$); 3.27-3.52 (m, 2H, CH$_{2\gamma'}$); 4.01-4.06 (m, 1H, CH$_\alpha$); 4.10-4.13 (t, 1H, CH$_{\alpha'}$); 5.02-5.03 (s, 2H, CH$_2$Ph); 5.19-5.25 (1H, J=6 Hz, NH); 7.24-7.29 (m, 5H, arom)

$^{13}$C NMR (CDCl$_3$, 75 MHz): 11.06; 16.04; 17.02; 18.21; 20.31; 21.39; 24.41; 25.40; 25.54; 26.55; 26.63; 26.80; 27.82; 28.46; 30.62; 31.34; 31.42; 39.42; 51.63; 56.97; 65.60; 72.78; 75.40; 79.31; 80.73; 81.00; 117.24; 123.48; 126.42; 126.82; 127.23; 135.16; 136.47; 136.66; 153.79; 154.78; 169.06; 169.60; 170.24.

The deprotection of the compound 7 followed by the protection-activation of the amine function of this deprotected compound are then carried out in the following way:

Palladium-on-carbon (150 mg, 30% by weight) is added to the compound 7 (0.48 g, 0.59 mmol) dissolved in anhydrous THF (7 mL). The air in the assembly is removed and replaced with argon by means of 3 argon-vacuum cycles, and then with hydrogen by means of 3 hydrogen-vacuum cycles. The reaction medium is left to stir vigorously for 6 hours and then filtered through celite and concentrated. The reaction mixture is dissolved in anhydrous dichloromethane (5 mL) and then triethylamine (0.20 mL, 1.18 mmol) is added, followed, dropwise, by 2,2,5,6,7-pentamethylchroman sulfonyl chloride (231 mg, 0.768 mmol) dissolved in anhydrous dichloromethane (4 mL), over the course of a period of 2 h. The reaction medium is left to stir vigorously overnight. The reaction medium is concentrated under vacuum and then taken up in ether (10 mL). The organic phase is successively washed with a 10% solution of citric acid (3×10 mL), with a saturated solution of sodium hydrogen carbonate (3×10 mL) and with distilled water (3×10 mL), and then dried over anhydrous magnesium sulfate and concentrated under vacuum. The disulfonamide 8 is obtained after silica gel chromatography (petroleum ether/ether 6/4) in the form of a colorless oil (480 mg, 86%).

The following compound 8 is obtained:

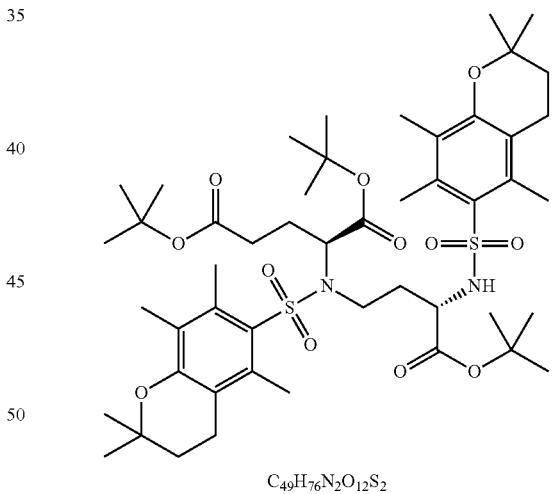

C$_{49}$H$_{76}$N$_2$O$_{12}$S$_2$

Rf: (petroleum ether/ether 6/4)=0.27
MS: [M+Na]$^+$, 971.6; [M+H]$^+$, 946.6; [M+H-tBu]$^-$, 893.5; [M+H-2 tBu]$^+$, 837.4; [M+H-3 tBu]$^+$, 781.3
$^1$H NMR (CDCl$_3$, 300 MHz): 1.13-1.33 (5s, 39H, 3 tBu, 6 CH$_3$); 1.71-1.82 (m, 4H, CH$_2$); 1.94-2.03 (m, 10H, 2 CH$_3$ meta, CH$_{2\beta}$, CH$_{2\beta'}$); 2.14-2.17 (t, 2H, CH$_{2\gamma}$); 2.41-2.42 (2s, 6H, 2 CH$_3$ ortho); 2.46-2.48 (2s, 6H, 2 CH$_3$ ortho); 2.55-2.59 (t, 4H, J=8.6 and 6.5 Hz, CH$_2$); 3.40-3.46 (t, 2H, J=7.9 and 8.7 Hz, CH$_{2\gamma'}$); 3.52-3.61 (m, 1H, CH$_\alpha$); 3.99-4.06 (m, 1H, CH$_{\alpha'}$); 5.19-5.22 (1H, J=8.3 Hz, NH)

$^{13}$C NMR (CDCl$_3$, 75 MHz): 12.30; 13.05; 13.15; 15.19; 18.19; 19.12; 19.15; 19.63; 20.30; 22.35; 22.44; 23.48; 26.37; 27.49; 27.51; 27.65; 28.42; 28.88; 29.91; 30.56; 32.55; 33.54;

34.08; 41.40; 55.11; 59.08; 74.84; 81.32; 82.67; 83.38; 103.68; 119.20; 119.38; 125.46; 125.51; 128.47; 129.24; 137.36; 137.56; 138.68; 138.76; 155.53; 155.84; 171.13; 171.40; 172.31.

A new alkylation of the compound 8 with the compound 4 is carried out in the following way:

Cesium carbonate (75 mg, 0.231 mmol) is added to a solution of the sulfonamide 8 (121 mg, 0.128 mmol) in anhydrous acetonitrile (600 µl) under an inert atmosphere. The reaction medium is stirred vigorously for 30 minutes, and is then heated to 55° C. Next, the iodinated compound 4 (107 mg, 0.256 mmol) in solution in anhydrous acetonitrile (600 µl) is added very slowly with a syringe driver. The reaction medium is left to stir vigorously at 55° C. overnight. The reaction medium is concentrated under vacuum and then taken up in cyclohexane (5 mL) The organic phase is washed with distilled water (3×5 mL), and then dried over anhydrous magnesium sulfate and concentrated under vacuum. The disulfonamide 9 is obtained after silica gel chromatography (dichloromethane/ether 97/3) in the form of a colorless oil (99 mg, 60%).

The following compound 9 is obtained:

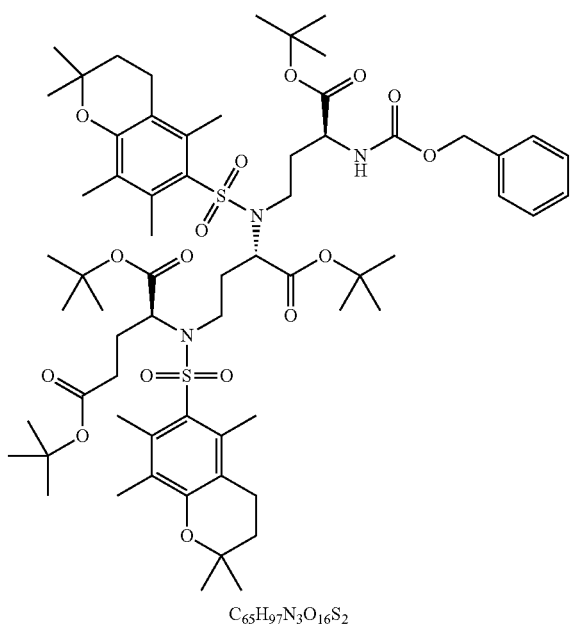

$C_{65}H_{97}N_3O_{16}S_2$

Rf: (dichloromethane/ether 96/4)=0.26

MS: [M+Na]$^+$, 1262.5; [M+H]$^+$, 1240.5; [M+H-tBu]$^+$, 1184.4; [M+H-2 tBu]$^+$, 1128.4; [M+H-3 tBu]$^+$, 1072.4; [M+H-4 tBu]$^+$, 1016.3

$^1$H NMR (CDCl$_3$, 300 MHz): 1.22-1.37 (5s, 48H, 3 tBu, 6 CH$_3$); 1.70-1.75 (t, 4H, J=6.4 and 6.7 Hz, CH$_2$); 1.78-2.04 (m, 12H, 2 CH$_3$ meta, CH$_{2\beta}$, CH$_{2\beta''}$, CH$_{2\beta'''}$); 2.17-2.20 (m, 2H, CH$_{2\gamma}$); 2.40-2.44 (2s, 6H, 2 CH$_3$ ortho); 2.46-2.48 (2s, 6H, 2 CH$_3$ ortho); 2.55-2.58 (t, 4H, J=6.5 and 6.6 Hz, CH$_2$); 3.33-3.44 (m, 4H, J=CH$_{2\gamma'}$, CH$_{2\gamma''}$); 3.95-4.03 (2m, 3H, CH$_\alpha$, CH$_{\alpha'}$, CH$_{\alpha''}$); 5.00-5.02 (d, 2H, J=6.8 Hz, CH$_2$Ph); 7.22-7.26 (m, 5H, arom)

$^{13}$C NMR (CDCl$_3$, 75 MHz): 12.30; 13.05; 13.15; 15.19; 18.19; 19.12; 19.15; 19.63; 20.30; 22.35; 22.44; 23.48; 26.37; 27.49; 27.51; 27.65; 28.42; 28.88; 29.91; 30.56; 32.55; 33.54; 34.08; 41.40; 55.11; 59.08; 74.84; 81.32; 82.67; 83.38; 103.68; 119.20; 119.38; 125.46; 125.51; 128.47; 129.24; 137.36; 137.56; 138.68; 138.76; 155.53; 155.84; 171.13; 171.40; 172.31.

Finally, the deprotection of the compound 9 is carried out in the following way:

Added to a Teflon reactor containing the compound 9 (79 mg, 0.064 mmol) are anisole (200 µl, 10% v/v) then hydrogen fluoride (2 mL, in excess) using a Teflon bench. The reaction medium is left to stir vigorously at 0° C. for 9 hours. The excess hydrogen fluoride is neutralized over potassium hydroxide. The residue is triturated from ether (3×3 mL) and then taken up in a 0.1 M hydrochloric acid solution. The water is removed by freeze-drying and the compound 10 is obtained pure in the form of a white solid.

The compound 10 is obtained, which is the nicotianamine derivative according to the invention having the following formula:

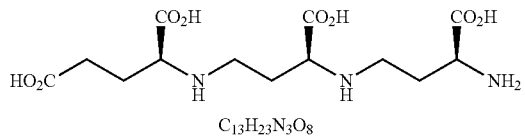

$C_{13}H_{23}N_3O_8$

MS: [M+H]$^+$, 350.1; [M−H-18]$^+$, 332.1

The invention claimed is:

1. A nicotianamine derivative, having the following formula:

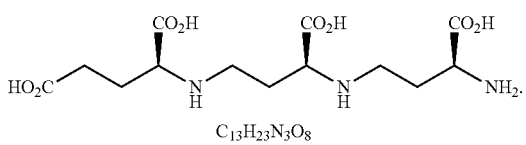

$C_{13}H_{23}N_3O_8$

2. A process for chemical synthesis of the nicotianamine derivative as claimed in claim 1, wherein the method comprises the following steps:
   a) protecting of the amine function of the α-tert-butyl ester of L-aspartic acid,
   b) reducing of the carboxylic function of the compound obtained in step a),
   c) halogenating of the alcohol function of the compound obtained in step b),
   d) protecting-activating of the amine function of the di-tert-butyl ester of L-glutamic acid,
   e) alkylating of the compound obtained in step d), with the compound obtained in step c),
   f) deprotecting followed by protection-activation of the amine function of the compound obtained in step e),
   g) alkylating of the compound obtained in step f), with the compound obtained in step c), and
   h) total deprotecting of the compound obtained in step g).

3. A process for enzymatic synthesis of the nicotianamine derivative as claimed in claim 1 by incubation of the substrates S-adenosylmethionine and glutamic acid in the presence of the MtNAS enzyme of *Methanothermobacter*.

4. The process of claim 2, wherein in step c) the alcohol function of the compound obtained in step b) is halogenated with iodine.

* * * * *